US009994675B2

(12) United States Patent
Williams et al.

(10) Patent No.: US 9,994,675 B2
(45) Date of Patent: *Jun. 12, 2018

(54) BIMETALLIC CATALYTIC COMPLEXES FOR THE POLYMERISATION OF CARBON DIOXIDE AND AN EPOXIDE

(71) Applicant: Imperial Innovations Limited, London (GB)

(72) Inventors: Charlotte K. Williams, London (GB); Michael Kember, London (GB); Paul Knight, Essex (GB)

(73) Assignee: Imperial Innovations Limited, London (GB)

( * ) Notice: Subject to any disclaimer, the term of this patent is extended or adjusted under 35 U.S.C. 154(b) by 137 days.

This patent is subject to a terminal disclaimer.

(21) Appl. No.: 14/526,017

(22) Filed: Oct. 28, 2014

(65) Prior Publication Data

US 2015/0051370 A1   Feb. 19, 2015

Related U.S. Application Data

(63) Continuation of application No. 12/989,537, filed as application No. PCT/GB2009/001043 on Apr. 24, 2009.

(51) Int. Cl.
| | |
|---|---|
| C08G 64/34 | (2006.01) |
| B01J 31/18 | (2006.01) |
| B01J 31/22 | (2006.01) |
| B01J 31/04 | (2006.01) |

(52) U.S. Cl.
CPC .......... *C08G 64/34* (2013.01); *B01J 31/1835* (2013.01); *B01J 31/226* (2013.01); *B01J 31/2239* (2013.01); *B01J 31/2243* (2013.01); *B01J 31/04* (2013.01); *B01J 2531/0216* (2013.01); *B01J 2531/0241* (2013.01); *B01J 2531/22* (2013.01); *B01J 2531/26* (2013.01); *B01J 2531/62* (2013.01); *B01J 2531/72* (2013.01); *B01J 2531/842* (2013.01); *B01J 2531/845* (2013.01)

(58) Field of Classification Search
None
See application file for complete search history.

(56) References Cited

U.S. PATENT DOCUMENTS

| 4,565,845 | A | 4/1986 | Inoue et al. |
|---|---|---|---|
| 4,665,134 | A | 5/1987 | Inoue et al. |
| 9,006,347 | B2 | 4/2015 | Williams et al. |
| 9,453,104 | B2 | 9/2016 | Williams et al. |
| 2006/0223973 | A1 | 10/2006 | Hinz et al. |
| 2011/0118435 | A1 | 5/2011 | Williams et al. |
| 2012/0172566 | A1 | 7/2012 | Zhang et al. |
| 2014/0249279 | A1 | 9/2014 | Williams et al. |
| 2016/0108181 | A1 | 4/2016 | Williams et al. |
| 2016/0347906 | A1 | 12/2016 | Williams et al. |

FOREIGN PATENT DOCUMENTS

| WO | WO 2008/128548 A2 | 10/2008 |
|---|---|---|
| WO | WO 2009/130470 A2 | 10/2009 |
| WO | WO 2009/137540 A1 | 11/2009 |
| WO | WO 2010/028362 A1 | 3/2010 |
| WO | WO 2010/110460 A1 | 9/2010 |
| WO | WO 2012/037282 A2 | 3/2012 |
| WO | WO 2013/034750 A2 | 3/2013 |

OTHER PUBLICATIONS

Sugimoto et al. Reactive & Functional Polymers, 67, 2007, 1277-1283.*
U.S. Appl. No. 12/989,537, filed Jan. 7, 2011, Williams et al.
U.S. Appl. No. 14/201,299, filed Mar. 7, 2014, Williams et al.
PCT/GB2009/001043, dated Jul. 7, 2009, International Search Report and Written Opinion.
PCT/GB2009/001043, dated Nov. 4, 2010, International Preliminary Report on Patentability.
Asato et al., Polynuclear zinc (II) complexes of phenol-imine and -amine macrocycles. J. Chem. Soc. Dalton Trans. 1995; 3897-3904.
Buchard et al., A bimetallic iron(III) catalyst for CO2/epoxide coupling. Chem Commun (Camb). Jan. 7, 2011;47(1):212-4. doi: 10.1039/c0cc02205e. Epub Sep. 27, 2010.
Kember et al., Highly active di- and trimetallic cobalt catalysts for the copolymerization of CHO and CO2 at atmospheric pressure. Macromolecules. 2010; 43(5):2291-98. doi: 10.1021/ma902582m.
Great Britain Search Report for GB 1308978.4, dated Nov. 14, 2013.
Great Britain Search Report for GB 1402109.1, dated Aug. 1, 2014.
International Search Report and Written Opinion for PCT/EP2012/067588, dated Mar. 14, 2013.
International Preliminary Report on Patentability for PCT/EP2012/067588, dated Mar. 20, 2014.
International Search Report and Written Opinion for PCT/GB2014/051511, dated Jan. 20, 2015.
International Preliminary Report on Patentability for PCT/GB2014/051511, dated Nov. 26, 2015.
International Search Report and Written Opinion for PCT/EP2015/052496, dated Apr. 7, 2015.
International Preliminary Report on Patentability for PCT/EP2015/052496, dated Aug. 18, 2016.
International Search Report and Written Opinion for PCT/GB2009/001043, dated Jul. 7, 2009.
International Preliminary Report on Patentability for PCT/GB2009/001043, dated Nov. 4, 2010.
Aida et al., Catalytic reaction on both sides of a metalloporphyrin plane. Alternating copolymerization of phthalic anhydride and epoxypropane with an aluminum porphyrin-quaternary salt system. J Am Chem Soc. 1985;107(5):1358-1364.

(Continued)

*Primary Examiner* — Yun Qian
(74) *Attorney, Agent, or Firm* — Wolf, Greenfield & Sacks, P.C.

(57) ABSTRACT

The present invention provides a novel catalyst of formula (I): wherein M is selected from Zn(H), Co(II), Mn(II), Mg(II), Fe(II), Cr(III)-X or Fe(III)-X, and the use thereof in polymerizing carbon dioxide and an epoxide.

9 Claims, 5 Drawing Sheets

(56) References Cited

OTHER PUBLICATIONS

Aida et al., Well-controlled polymerization by metalloporphyrin. Synthesis of copolymer with alternating sequence and regulated molecular weight from cyclic acid anhydride and epoxide catalyzed by the system of aluminum porphyrin coupled with quaternary organic salt. Macromolecules. 1985;18:1049.

Allen et al., High-activity, single-site catalysts for the alternating copolymerization of CO2 and propylene oxide. J Am Chem Soc. Dec. 4, 2002;124(48):14284-5.

Black et al., Compartmental Schiff-base ligands as selective double-loaded extractants for copper(II). Chem Commun (Camb). Feb. 21, 2002;(4):340-1.

Bok et al., Bimetallic fluorine-substituted anilido-aldimine zinc complexes for CO2/(cyclohexene oxide) copolymerization. Inorg Chem. May 15, 2006;45(10):4228-37.

Bradley et al., Homometallic Alkoxides. Alkoxo and Aryloxo Derivatives of Metals. Elsevier. 2001; 1:105-109.

Chamberlain et al., Polymerization of lactide with zinc and magnesium beta-diiminate complexes: stereocontrol and mechanism. J Am Chem Soc. Apr. 11, 2001;123(14):3229-38.

Cheng et al., Catalytic Reactions Involving C1 Feedstocks: New High-Activity Zn(II)-Based Catalysts for the Alternating Copolymerization of Carbon Dioxide and Epoxides. J Am Chem Soc. 1998;120:11018-19.

Cheng et al., Single-site beta-diiminate zinc catalysts for the alternating copolymerization of CO2 and epoxides: catalyst synthesis and unprecedented polymerization activity. J Am Chem Soc. Sep. 12, 2001;123(36):8738-49.

Coates et al., Discrete Metal-Based Catalyst for the Copolymerization of CO2 and Epoxides: Discovery, Reactivity, Optimization, and Mechanism. Angew Chem Int Ed. 2004;43:6618-39.

Cyriac et al., Immortal CO2/Propylene Oxide Copolymerization: Precise Control of Molecular and Weight and Architecture of Various Block Copolymers. Macromolecules. 2010;43(18):7398-401.

Darensbourg et al., Bis 2,6-difluorophenoxide Dimeric Complexes of Zinc and Cadmium and Their Phosphine Adducts :Lessons Learned Relative to Carbon Dioxide/Cyclohexene Oxide Alternating Copolymerization Processes by Zinc Phenoxides. J Am Chem Soc. 2000;122:12487-96.

Darensbourg et al., Catalytic Activity of a Series of Zn(II) Phenoxides for the Copolymerization of Epoxides and Carbon Dioxides. J Am Chem Soc. 1999;121:107-16.

Darensbourg et al., Kinetic Studies of the Alternating Copolymerization of Cyclic Acid Anhydrides and Epoxides, and the Terpolymerization of Cyclic Acid Anhydrides, Epoxides, and CO2 Catalyzed by (salen)CrIIICl. Macromolecules. 2012;45(5):2242-48.

Darensbourg et al., Mechanistic aspects of the copolymerization reaction of carbon dioxide and epoxides, using a chiral salen chromium chloride catalyst. J Am Chem Soc. Jun. 5, 2002;124(22):6335-42.

Darensbourg et al., Solution and solid-state structures of phosphine adducts of monomeric zinc bisphenoxide complexes. Importance of these derivatives in CO2/epoxide copolymerization processes. Inorg Chem. Apr. 3, 2000;39(7):1578-85.

Darensbourg, Making plastics from carbon dioxide: salen metal complexes as catalysts for the production of polycarbonates from epoxides and CO2. Chem Rev. Jun. 2007;107(6):2388-410. Epub Apr. 21, 2007.

Das et al., Iso- and mixed-valent phenoxy bridged binuclear macrocyclic complexes of cobalt, iron and manganese. Polyhedron. 1994;13(38):2639-45.

Diciccio et al., Ring-Opening Copolymerization of Maleic Anhydride with Epoxides: A Chain-Growth Approach to Unsaturated Polyesters. J Am Chem Soc. 2011;133:10724-27.

Dutta et al., Efficient proton-templated synthesis of 18- to 38-membered tetraimino(amino)diphenol macrocyclic ligands: structural features and spectroscopic properties. J Org Chem. Aug. 6, 2004;69(16):5419-27.

Dutta et al., Model Compounds for Iron Proteins. Structures and Magnetic, Spectroscopic, and Redox Properties of Fe(III)M(II) and [Co(III)Fe(III)](2)O Complexes with (&mgr;-Carboxylato)bis( &mgr;-phenoxo)dimetalate and (&mgr;-Oxo)diiron(III) Cores. Inorg Chem. Apr. 10, 1996;35(8):2292-2300.

Eberhardt et al., The Ethylsulfinate Ligand: A Highly Efficient Initiating Group for the Zinc β-Diiminate Catalyzed Copolymerization of CO2 and Epoxides. Organometallics. 2003;22:211-14.

Hosseini et al., Alternating Ring-Opening Polymerization of Cyclohexene Oxide and Anhydrides: Effect of Catalyst, Cocatalyst, and Anhydride Structure. Macromolecules. 2012;45(4):1770-76.

Hosseini et al., Interaction energy and polymer density profile in nanocomposites: a coarse grain simulation based on interaction stress. Polym Chem. 2012;3:1158-67.

Inoue et al., Copolymerization of carbon dioxide and epoxide. Polymer Letts. 1969;7:287-92.

Inoue et al., Immortal polymerization: the outset, development, and application. J Polym. Sci. Part A Polym. Chem. 2000;38:2861-71.

Jeske et al., Alternating copolymerization of epoxides and cyclic anhydrides: an improved route to aliphatic polyesters. J Am Chem Soc. Sep. 19, 2007;129(37):11330-1. Epub Aug. 28, 2007.

Jutz et al., Mechanistic Investigation and Reaction Kinetics of the Low-Pressure Copolymerization of Cyclohexene Oxide and Carbon Dioxide Catalyzed by a Dizinc Complex. J Am Chem Soc. 2011;133(43):17395-17405.

Kember et al., Di- and tri-zinc catalysts for the low-pressure copolymerization of CO2 and cyclohexene oxide. Inorg Chem. Oct. 5, 2009;48(19):9535-42. doi: 10.1021/ic901109e.

Kember et al., Di-cobalt(II) catalysts for the copolymerisation of CO2 and cyclohexene oxide: support for a dinuclear mechanism? Chem Sci. 2012;3:1245-55.

Kember et al., Efficient Magnesium Catalysts for the Copolymerization of Epoxides and CO2; Using Water to Synthesize Polycarbonate Polyols. J Am Chem Soc. 2012;134(38):15676-15679.

Kember et al., Highly active dizinc catalyst for the copolymerization of carbon dioxide and cyclohexene oxide at one atmosphere pressure. Angew Chem Int Ed Engl. 2009;48(5):931-3.

Kember et al., Triblock copolymers from lactide and telechelic poly(cyclohexene carbonate). Polym Chem. 2012;3:1196-1201.

Knight et al., Dinuclear zinc complexes using pentadentate phenolate ligands. Inorg Chem. Dec. 15, 2008;47(24):11711-9.

Koning et al., Synthesis and physical characterization of poly(cyclohexane carbonate), synthesized from CO2 and cyclohexene oxide. Polymer. 2001;42:3995-4004.

Lee et al., Bimetallic anilido-aldimine zinc complexes for epoxide/CO2 copolymerization. J Am Chem Soc. Mar. 9, 2005;127(9):3031-7.

Lu et al., Design of highly active binary catalyst systems for CO2/epoxide copolymerization: polymer selectivity, enantioselectivity, and stereochemistry control. J Am Chem Soc. Feb. 8, 2006;128(5):1664-74.

Moore et al., Mechanism of the alternating copolymerization of epoxides and CO2 using beta-diiminate zinc catalysts: evidence for a bimetallic epoxide enchainment. J Am Chem Soc. Oct. 1, 2003;125(39):11911-24.

Nozaki et al., Asymmetric catalytic synthesis of polyketones and polycarbonates. Pure Appl Chem. 2004;76(3):541-46.

Paddock et al., Chemical CO(2) fixation: Cr(III) salen complexes as highly efficient catalysts for the coupling of CO(2) and epoxides. J Am Chem Soc. Nov. 21, 2001;123(46):11498-9.

Pilz et al., Dinuclear Zinc Complexes Based on Parallel β-Diiminato Binding Sites: Syntheses, Structures, and Properties as CO2/Epoxide Copolymerization Catalysts. Organometallics. 2007;26:3668-76.

Qin et al., Cobalt-Based Complexes for the Copolymerization of Propylene Oxide and CO2; Active and Selective Catalysts for Polycarbonate Synthesis. Angew Chem Int Ed. 2003;42:5484-87.

Ren et al., Highly Active, Bifunctional Co(III)-Salen Catalyst for Alternating Copolymerization of CO2 with Cyclohexene Oxide and Terpolymerization with Aliphatic Epoxides. Macromolecules. 2010;43(3):1396-1402.

(56) References Cited

OTHER PUBLICATIONS

Robert et al., Tandem synthesis of alternating polyesters from renewable resources. Nature Comm. 2011;2:586.

Rokicki et al., The Application of Carbon Dioxide as a Direct Material for Polymer Syntheses in Polymerization and Polycondensation Reactions. J Macromol Sci Rev Macomol Chem Phys 1981;C21(1):135-86.

Saini et al., Dinuclear metal catalysts: improved performance of heterodinuclear mixed catalysts for CO2-epoxide copolymerization. Chem Commun. 2014;50:4164-67.

Sugimoto et al., Alternating Copolymerization of Carbon Dioxide and Epoxide by Manganese Porphyrin: The First Example of Polycarbonate Synthesis from 1-atm Carbon Dioxide. J Polym Sci Polym Chem. 2003;41:3549-55.

Sugimoto et al., Copolymerization of Carbon Dioxide and Epoxide. J Polym Sci Polym Chem. 2004;42:5561-73.

Sugimoto et al., The Cobalt Porphyrin-Lewis Base System: A Highly Selective Catalyst for Alternating Copolymerization of CO2 and Epoxide under Mild Condition. Macromolecules. 2008;41:312-17.

Van Meerendonk et al., High-Throughput Automated Parallel Evaluation of Zinc-Based Catalysts for the Copolymerization of CHO and CO2 to Polycarbonates. Macromol Rapid Commun. 2004;25:382-86.

Van Meerendonk et al., Unexpected Side Reactions and Chain Transfer for Zinc-Catalyzed Copolymerization of Cyclohexene Oxide and Carbon Dioxide. Macromolecules. 2005;38:7306-13.

Williams et al., A highly active zinc catalyst for the controlled polymerization of lactide. J Am Chem Soc. Sep. 17, 2003;125(37):11350-9.

Williams et al., Metalloenzyme inspired dizinc catalyst for the polymerization of lactide. Chem Commun (Camb). Sep. 21, 2002;(18):2132-3.

Wu et al., Tandem metal-coordination copolymerization and organocatalytic ring-opening polymerization via water to synthesize diblock copolymers of styrene oxide/CO2 and lactide. J Am Chem Soc. Oct. 24, 2012;134(42):17739-45. doi: 10.1021/ja307976c. Epub Oct. 9, 2012.

Xiao et al., Copolymerization of cyclohexene oxide with CO2 by using intramolecular dinuclear zinc catalysts. Chemistry. Jun. 6, 2005;11(12):3668-78.

Xiao et al., Intramolecularly Dinuclear Magnesium Complex Catalyzed Copolymerization of Cyclohexene Oxide with CO2 under Ambient CO2 Pressure: Kinetics and Mechanism. Macromolecules. 2006;39:128-37.

\* cited by examiner

BIMETALLIC CATALYTIC COMPLEXES FOR THE POLYMERISATION OF CARBON DIOXIDE AND AN EPOXIDE

RELATED APPLICATIONS

The present application is a continuation of and claims priority under 35 U.S.C. § 120 to U.S. application, U.S. Ser. No. 12/989,537, filed Jan. 7, 2011, which is a national stage filing under 35 U.S.C. § 371 of international PCT application, PCT/GB2009/001043, filed Apr. 24, 2009, which claims priority to United Kingdom application number 0807607.7, filed Apr. 25, 2008, the entire contents of each of which are incorporated herein by reference.

The present invention provides a novel catalyst and its use in the co-polymerisation of carbon dioxide and an epoxide.

Carbon dioxide is an attractive reagent for synthetic chemistry as it is abundant, inexpensive, of low toxicity and the waste product of many chemical processes. The copolymerization of carbon dioxide and epoxides, known for several decades as illustrated in FIG. 1, is a particularly promising route to activate and use $CO_2$ as a renewable C-1 source. Furthermore, if cyclohexene oxide is used, the copolymer has a high glass transition temperature and tensile strength, but is also degradable.

The first report of the copolymerization of carbon dioxide and an epoxide was reported by Inoue et al, in 1969 using diethyl zinc and alcohols to produce poly(propylene carbonate), albeit with very low turn-over numbers (TON). Subsequently several research groups developed more active and controlled catalysts, including zinc phenoxide, zinc β-diiminate and chromium(III) or cobalt(III) salen complexes and various bimetallic zinc catalysts, including anilido aniline zinc catalysts. The zinc β-diiminate complexes show very high turn-over frequencies (TOF), as well as excellent control for the copolymerization of $CO_2$ and cyclohexene oxide.

However, the copolymerization of carbon dioxide and an epoxide currently requires the use of high pressures in order to achieve the necessary turn over numbers and turn over frequencies. Furthermore, the use of such air sensitive catalysts requires the use of special handling techniques to avoid deactivation of the catalyst. There is therefore a need in the art for improved catalysts to allow use of carbon dioxide as a renewable C-1 source.

There is therefore provided by the first aspect of the invention a catalyst of formula (I)

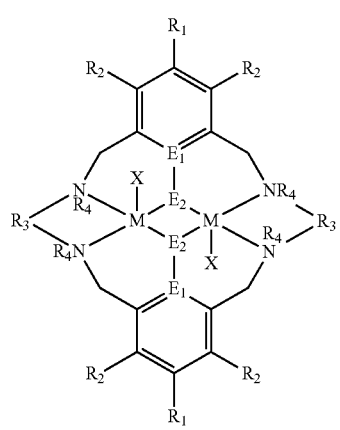

(I)

wherein $R_1$ and $R_2$ are independently hydrogen, alkyl, haloalkyl, aryl, halide, amine, a nitro group, an ether group, a silyl ether group, a nitrile group or an acetylide group;
$R_3$ is alkylene, arylene or cycloalkylene;
$R_4$ is H, alkyl, aryl or alkylaryl;
$E_1$ is C, $E_2$ is O, S or NH or $E_1$ is N and $E_2$ is O;
X is $OCOCH_3$, $OCOCF_3$, $OSO_2C_7H_7$, $OSO(CH_3)_2$, alkyl, alkoxy, halide or amido;
M is Zn(II), Co(II), Mn(II), Mg (II), Fe(II), Cr(II), Cr (III)-X, Co(III)-X, Mn(III)-X or Fe(III)-X.

For the purpose of the present invention, an alkyl group is preferably a "$C_{1-6}$ alkyl group", that is an alkyl group that is a straight or branched chain with 1 to 6 carbons. The alkyl group therefore has 1, 2, 3, 4, 5 or 6 carbon atoms. Specifically, examples of "$C_{1-6}$ alkyl group" include methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

A cycloalkyl group is preferably a "$C_{3-8}$ cycloalkyl group" that is a cycloalkyl group with 3 to 8 carbon atoms. The cycloalkyl group therefore has 3, 4, 5, 6, 7 or 8 carbon atoms. Specifically, examples of the $C_{3-8}$ cycloalkyl group include cyclopropyl, cyclobutyl, cyclopentyl, cyclohexyl, cycloheptyl and cyclooctyl. It will be appreciated that the cycloalkyl group may comprise a cycloalkyl ring bearing one or more linking or non-linking alkyl substituents, such as —$CH_2$-cyclohexyl.

The term "halide" used herein means a fluorine atom, a chlorine atom, a bromine atom, an iodine atom and the like, preferably a fluorine atom or a chlorine atom, and more preferably a fluorine atom.

A haloalkyl group is preferably a "$C_{1-6}$ haloalkyl group" and is a $C_{1-6}$ alkyl group as described above substituted with 1, 2 or 3 halogen atom(s). Specifically, examples of "$C_{1-6}$ haloalkyl group" include fluoromethyl group, difluoromethyl group, trifluoromethyl group, fluoroethyl group, difluoroethyl group, trifluoroethyl group, chloromethyl group, bromomethyl group, iodomethyl group and the like.

An alkoxy group is preferably a "$C_{1-6}$ alkoxy group" and is an oxy group that is bonded to the previously defined "$C_{1-6}$ alkyl group". Specifically, examples of "$C_{1-6}$ alkoxy group" include methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-1 dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like. Specifically, examples of "$C_{6-10}$ aryl group" include phenyl group, biphenyl group, indenyl group, naphthyl group or azulenyl group and the like. It should be noted that condensed rings such as indan and tetrahydro naphthalene are also included in the aryl group.

An alkylaryl group is preferably a "$C_{1-16}$ alkyl $C_{6-12}$ aryl group" and is an aryl group as defined above bonded at any position to an alkyl group as defined above. Preferably, the alkylaryl group is —$CH_2$-Ph or —$CH_2CH_2$-Ph.

An ether group is preferably a group $OR_5$ wherein $R_5$ can be an alkyl group or an aryl group as defined above. Preferably, $R_5$ is an alkyl group selected from methyl, ethyl or propyl.

A silyl ether group is preferably a group $OSi(R_6)_3$ wherein each $R_6$ can be independently an alkyl group or an aryl group as defined above. Preferably, each $R_6$ is an alkyl group selected from methyl, ethyl or propyl.

A nitrile group is preferably a group CN or a group $CNR_7$ wherein $R_7$ is an alkyl group or an aryl group as defined above. Preferably $R_7$ is an alkyl group selected from methyl, ethyl or propyl.

An alkenyl group contains a double bond —C=C—$R_8$ wherein $R_8$ can be an alkyl group or an aryl group as defined above. For the purposes of the invention when $R_8$ is alkyl, the double bond can be present at any position along the alkyl chain. Preferably $R_8$ is methyl, ethyl, propyl or phenyl.

An acetylide group contains a triple bond —C≡C—$R_9$, wherein $R_9$ can be an alkyl group or an aryl group as defined above. For the purposes of the invention when $R_9$ is alkyl, the triple bond can be present at any position along the alkyl chain. Preferably $R_9$ is methyl, ethyl, propyl or phenyl.

An amino group is preferably $NH_2$, $NHR_{10}$ or $N(R_{10})_2$ wherein $R_{10}$ can be an alkyl group, a silylalkyl group or an aryl group as defined above. It will be appreciated that when the amino group is $N(R_{10})_2$, each $R_{10}$ group can be independently selected from an alkyl group, a silylalkyl group or an aryl group as defined above. Preferably $R_{10}$ is methyl, ethyl, propyl, $SiMe_3$ or phenyl.

An amido group is —$NR_{11}C(O)$— or —$C(O)$—$NR_{11}$— wherein $R_{11}$ can be hydrogen, an alkyl group or an aryl group as defined above. Preferably $R_{11}$ is hydrogen, methyl, ethyl, propyl or phenyl.

It will be appreciated that for the catalyst of the first aspect, the groups $R_1$ and $R_2$ may be the same or different. For the purposes of the present invention, $R_1$ and $R_2$ are preferably independently selected from hydrogen, tBu, Me, $CF_3$, phenyl, F, Cl, Br, I, $NMe_2$, $NEt_2$, $NO_2$, OMe, $OSiEt_3$, CNMe, CN or CCPh, more preferably hydrogen, OMe, Me or tBu (e.g. hydrogen or tBu). In certain embodiments, $R_2$ is hydrogen and $R_1$ is any one of the groups defined above, preferably tBu, OMe or Me.

It will be appreciated that the group $R_3$ is a disubstituted alkyl, aryl or cycloalkyl group which acts as a bridging group between two nitrogen centres in the catalyst of formula (I). Thus, where $R_3$ is a alkylene group, such as dimethylpropylene, the $R_3$ group has the structure —$CH_2$—$C(CH_3)_2$—$CH_2$—. The definitions of the alkyl, aryl and cycloalkyl groups set out above therefore also relate respectively to the alkylene, arylene and cycloalkylene groups set out for $R_3$. Preferably $R_3$ is ethylene, 2,2-dimethylpropylene, propylene, butylene, phenylene, cyclohexylene or biphenylene, more preferably 2,2-dimethylpropylene. When $R_3$ is cyclohexylene, it can be the racemic, RR- or SS- forms.

Preferably $R_4$ is H, Me, Et, Bn, iPr, tBu or Ph, more preferably hydrogen.

Preferably X is $OCOCH_3$, $OCOCF_3$, $OSO_2C_7H_7$, $OSO(CH_3)_2$, Et, Me, PhOEt, OMe, OiPr, OtBu, Cl, Br, I, F, $N(iPr)_2$ or $N(SiMe_3)_2$, more preferably $OCOCH_3$.

Preferably M is Zn(II), Cr(III), Cr(II), Co(III), Co(II), Mn(III), Mn(II), Mg (II), Fe(II) or Fe(III), more preferably Zn(II), Cr(III), Co(II), Mn(II), Mg(II), Fe(II) or Fe(III), and most preferably Zn(II) or Mg(II). It will be appreciated that when M is Cr(III), Co(III), Mn(III) or Fe (III), the catalyst of formula (I) will contain an additional X group co-ordinated to the metal centre, wherein X is as defined above.

In a particularly preferred aspect of the first aspect of the invention, there is provided a catalyst selected from:

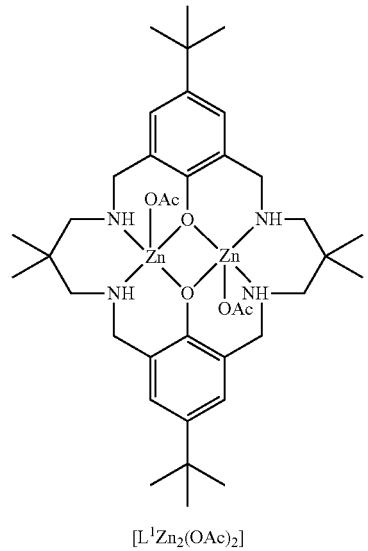

[$L^1Zn_2(OAc)_2$]

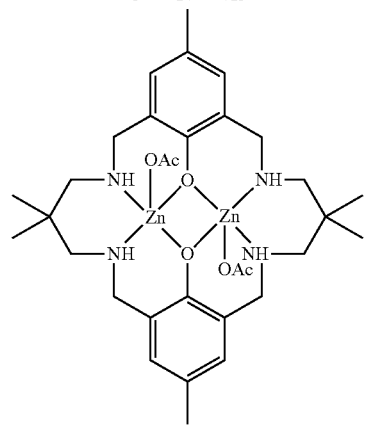

[$L^2Zn_2(OAc)_2$]

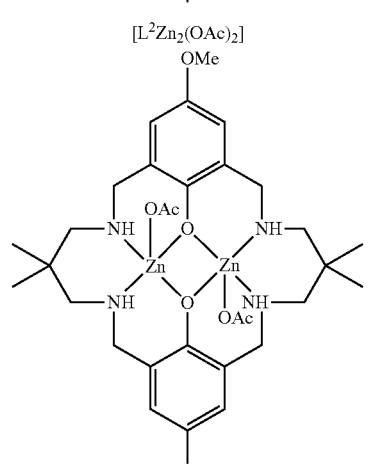

[$L^3Zn_2(OAc)_2$]

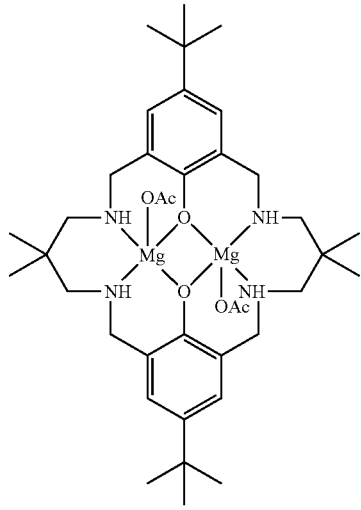

[L¹Mg₂(OAc)₂]

A catalyst of formula (I) of the first aspect of the invention may be prepared by complexation of a ligand (for example $H_2L^1$, $H_2L^2$ or $H_2L^3$, where $L^1$, $L^2$ or $L^3$ are as represented within the structures shown above) with a metal complex comprising the groups M and X. Carrying out this complexation in the presence of water where X is $OCOCH_3$, $OCOCF_3$, $OSO_2C_7H_7$, $OSO(CH_3)_2$ or halide may lead, in addition to the formation of a catalyst of formula (I), to the formation of a dimeric catalyst species comprising two catalyst complexes of formula (I), linked by a bridging ligand X, with a bound water molecule. Accordingly, in a second aspect the invention provides a dimeric catalyst formed from two of the same monomeric subunits and a bound water molecule, wherein each monomeric subunit is a catalyst of formula (I) of the first aspect of the invention wherein X is $OCOCH_3$, $OCOCF_3$, $OSO_2C_7H_7$, $OSO(CH_3)_2$ or halide, and wherein the two monomeric subunits are linked by a bridging ligand X. The bridging group X may bridge between one M of each monomeric subunit, with a water molecule being bound to an M of one monomeric subunit. Each monomeric subunit of formula (I) which forms the dimeric complex has the same structure (i.e. each subunit has the same group at the $R_1$, $R_2$, $R_3$, $R_4$, $E_1$, $E_2$ and M positions, respectively).

The dimeric catalyst of the second aspect can be illustrated by the formula (II):

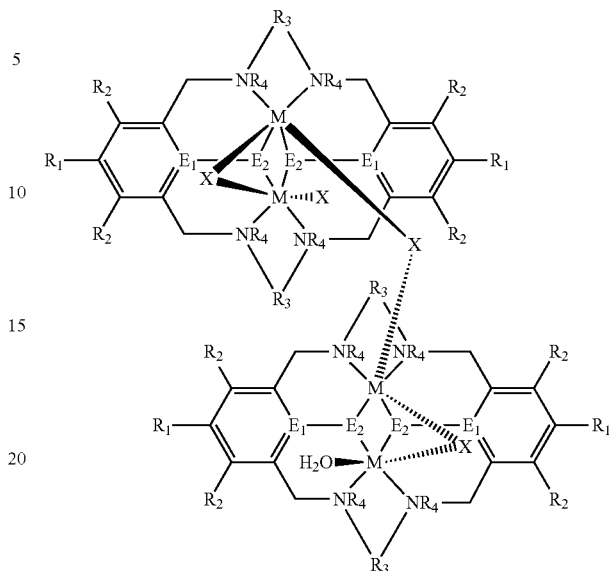

(II)

wherein the groups $R_1$, $R_2$, $R_3$, $R_4$, $E_1$, $E_2$ and M are as defined for the first aspect of the invention and X is $OCOCH_3$, $OCOCF_3$, $OSO_2C_7H_7$, $OSO(CH_3)_2$ or halide. Preferably X is $OCOCH_3$, $OCOCF_3$, $OSO_2C_7H_7$ or $OSO(CH_3)_2$ and more preferably $OCOCH_3$.

M is preferably Zn(II) or Mg(II), more preferably Mg(II).

In a particularly preferred aspect of the second aspect of the invention, there is provided a catalyst as illustrated below:

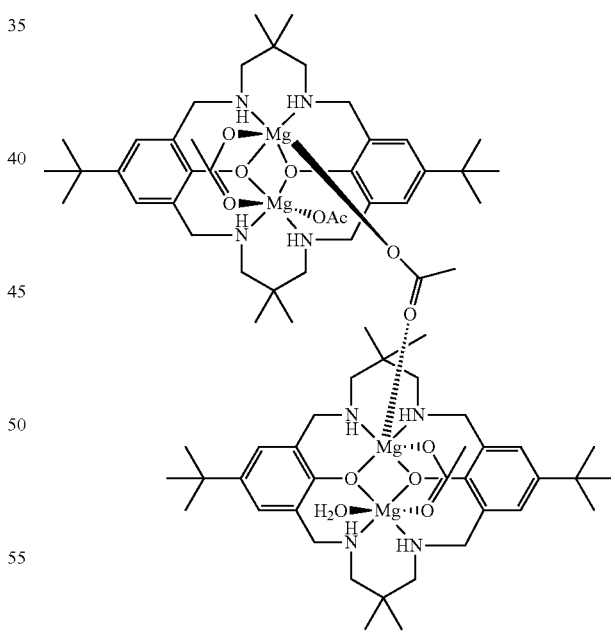

When a ligand (for example $H_2L^1$, $H_2L^2$ or $H_2L^3$) is combined with a metal complex comprising the groups M and X, in the presence of water, the product formed may be a mixture of the catalyst of formula (I) of the first aspect and the dimeric catalyst of the second aspect of the invention, wherein X is $OCOCH_3$, $OCOCF_3$, $OSO_2C_7H_7$, $OSO(CH_3)_2$ or halide. Accordingly, a third aspect of the invention provides a mixture of the catalytic species of the first aspect and the second aspect of the invention.

The fourth aspect of the invention provides a process for the reaction of carbon dioxide with an epoxide in the presence of a catalyst of the first aspect, the second aspect or the third aspect of the invention.

For the purposes of the present invention, the epoxide substrate is not limited. The term epoxide therefore relates to any compound comprising an epoxide moiety. Preferred examples of epoxides for the purposes of the present invention include cyclohexene oxide, propylene oxide, substituted cyclohexene oxides (such as limonene oxide, $C_{10}H_{16}O$ or 2-(3,4-epoxycyclohexyl) ethyltrimethoxysilane, $C_{11}H_{22}O$), alkylene oxides (such as ethylene oxide and substituted ethylene oxides) or substituted oxiranes (such as epichlorohydrin, 1,2-epoxybutane, glycidyl ethers).

The process of the fourth aspect of the invention is particularly provided for the reaction of carbon dioxide with an epoxide at low pressures. The reaction can therefore be carried out at a pressure of 1 to 10 atmospheres, preferably at 1 or 2 atmospheres.

The process of the fourth aspect of the invention can be carried out at a temperature of 50° C. to 100° C. The duration of the process can be up to 48 hours preferably 20 to 24 hours.

The process of the fourth aspect of the invention can advantageously be carried out at low catalytic loading, for example, the catalytic loading for the process is preferably in the range of 1:1000-10000 catalyst:epoxide, more preferably in the region of 1:1000 catalyst:epoxide, and most preferably in the region of 1:10000 catalyst:epoxide.

The present invention provides a bimetallic catalytic complex and allows the reaction of epoxides with carbon dioxide with high turn over numbers and turn over frequencies.

It should be noted that the catalysts of the present invention operate at remarkably low pressure, e.g. 1 atm of $CO_2$. Indeed, the catalysts show comparable TON and TOF to literature catalysts but operate at 1/60 of the pressure of $CO_2$.

In addition, unlike conventional catalysts, most of the catalysts of the present invention are air stable and do not require the special handling associated with the conventional air sensitive catalysts.

The fifth aspect of the invention provides a product of the process of the fourth aspect of the invention.

The sixth aspect of the invention provides a process for the production of a catalyst of the first aspect of the invention, said process comprising reaction of a compound of formula (III)

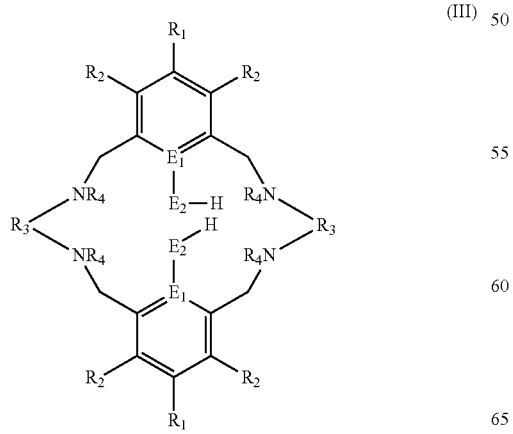

(III)

with a metal complex comprising the groups M and X, wherein the groups $R_1$, $R_2$, $R_3$, $R_4$, M, X, $E_1$ and $E_2$ are as defined for the first aspect of the invention. It will be appreciated that when $E_1$ is N and $E_2$ is =O, the H atom is absent from the $E_2$—H group illustrated for the compound of formula (III).

For the purposes of this invention the number of the groups X present in the metal complex will depend on the valency of the metal M. For example, wherein M is Zn(II) and X is OAc, the metal complex will be $Zn(OAc)_2$. Alternatively, the metal complex may have the formula M-XH.

For the purposes of the sixth aspect of the invention, the reaction of the compound of formula (III) with a metal complex can be carried out in the presence or absence of a base. Where the reaction is carried out in the presence of a base, the base can be selected from one or more of an amine base, such as $Et_3N$ or a hydride base, such as NaH, LiH or KH.

The reaction of the compound of formula (III) with a metal complex can be carried out in a solvent (for example THF, toluene, dichloromethane or methanol). The solvent is preferably anhydrous.

In certain embodiments, the process is carried out under anhydrous conditions and preferably the metal complex is anhydrous.

It will be appreciated that a process as defined in the sixth aspect of the invention may be used to produce a catalyst of the second or third aspect of the invention, wherein X is $OCOCH_3$, $OCOCF_3$, $OSO_2C_7H_7$, $OSO(CH_3)_2$ or halide, by the inclusion of water within the reaction, for example by providing a metal complex which is not completely anhydrous.

The seventh aspect of the invention provides a ligand as illustrated below:

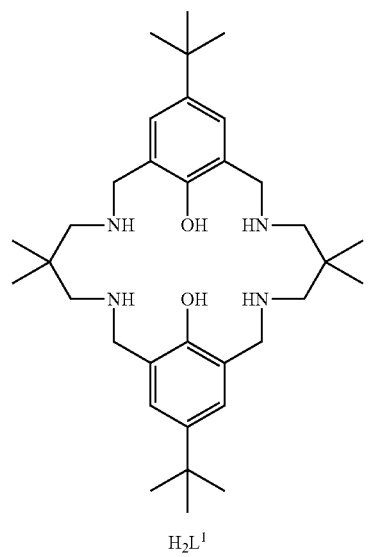

$H_2L^1$

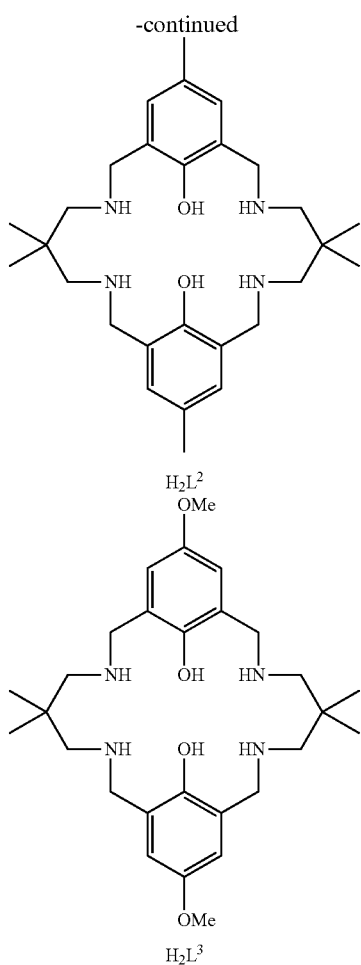

H₂L²

H₂L³

The ligand of the seventh aspect of the invention is provided for use in the production of a catalyst of the first, second or third aspects of the invention. The seventh aspect of the invention therefore further provides a process for the production of a catalyst of the first aspect of the invention, said process comprising reaction of the ligand of the seventh aspect of the invention with a metal complex comprising the groups M and X as defined in the first aspect of the invention. The seventh aspect of the invention yet further provides a process for the production of a catalyst of the second or third aspects of the invention, said process comprising reaction of the ligand of the seventh aspect of the invention with a metal complex comprising the groups M and X, wherein X is $OCOCH_3$, $OCOCF_3$, $OSO_2C_7H_7$, $OSO(CH_3)_2$ or halide, wherein the reaction is carried out in the presence of water, for example by providing a metal complex which is not completely anhydrous. In certain embodiments, the process for the production of a catalyst of the first, second or third aspects of the invention is carried out in a solvent (for example THF, toluene, dichloromethane or methanol), preferably wherein the solvent is anhydrous. The process for the production of a catalyst of the first, second or third aspects of the invention may be carried out in the presence of KH. For the purposes of the seventh aspect of the invention, the metal complex is preferably $Zn(OAc)_2$ or $Mg(OAc)_2$.

All preferred features of each of the aspects of the invention apply to all other aspects mutatis mutandis.

The invention may be put into practice in various ways and a number of specific embodiments will be described by way of example to illustrate the invention with reference to the accompanying drawings, in which.

EXAMPLES

Example 1

Figure 2:
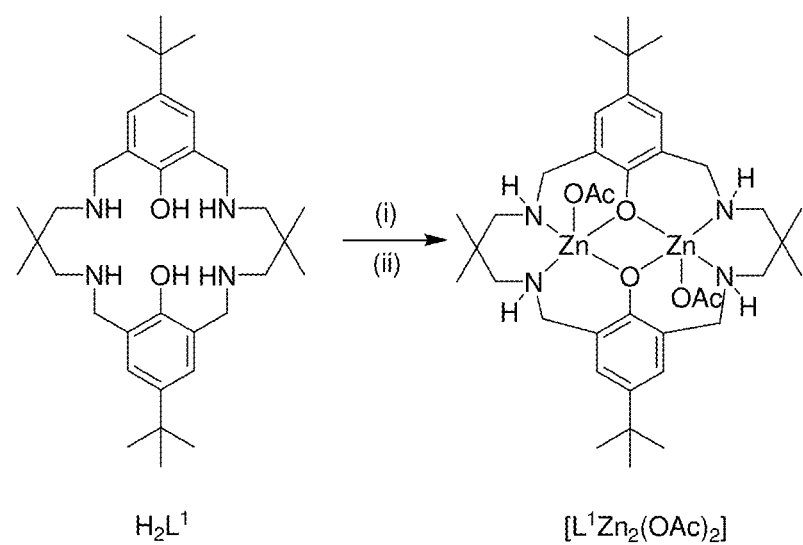
FIG. 2 shows the synthesis of the dizinc complex $[L^1Zn_2(OAc)_2]$. Reagents and conditions: i) KH, THF, $-78°$ C.→RT, 1 hour. ii) $Zn(OAc)_2$, THF, RT, 16 hours.

Reaction of a number of epoxides with carbon dioxide were carried out using a bimetallic zinc complex $[L^1Zn_2(OAc)_2]$ as illustrated in FIG. 2. The macrocyclic ligand, $H_2L^1$, was prepared two steps, in 84% overall yield, from commercial reagents as described below. The bimetallic zinc complex, $[L^1Zn_2(OAc)_2]$, was prepared by the double deprotonation of the $H_2L^1$, using potassium hydride, and the subsequent reaction with zinc acetate. The complex was isolated, as a white solid, in 70% yield.

Figure 4:
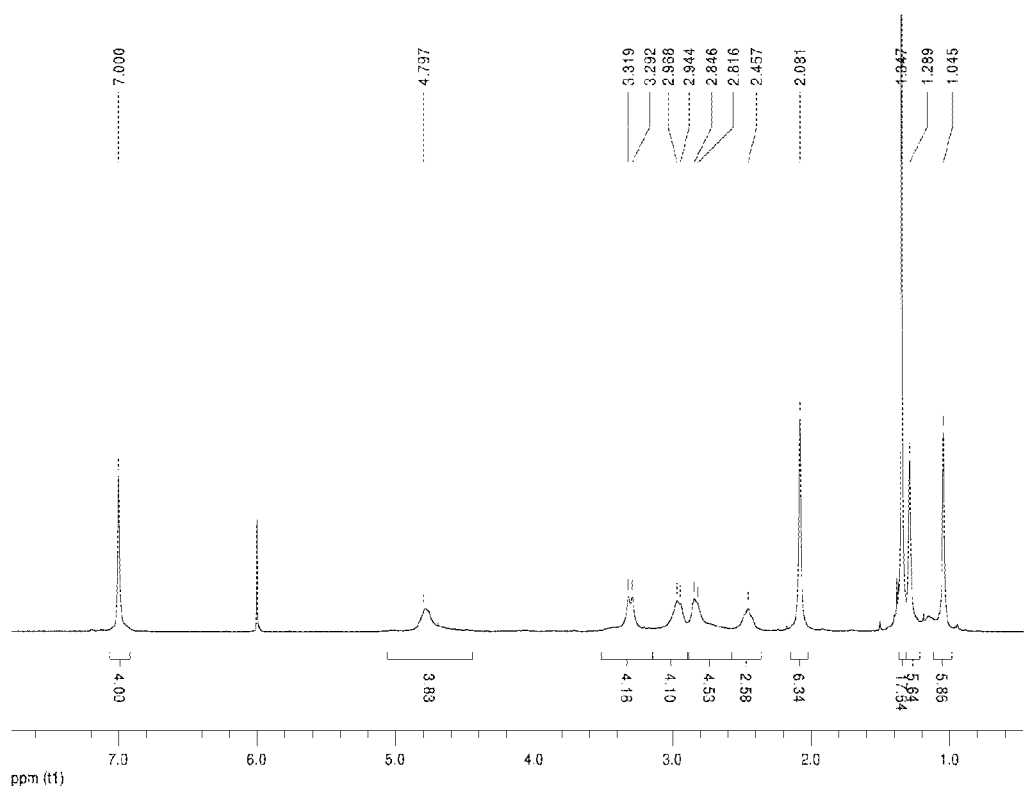
FIG. 4 shows a $^1$H NMR spectrum, at $110°$ C. of the dizinc complex $[L^1Zn_2(OAc)_2]$.

The complex stoichiometry was confirmed by the elemental analysis being in excellent agreement with the calculated values and a daughter peak in the FAB mass spectrum for the molecular ion less an acetate group. The $^1$H NMR spectrum, at $25°$ C., shows several broadened resonances, consistent with the several diastereoisomers being present, which are fluxional on the NMR timescale. When the sample was heated to $110°$ C., coalescence was observed as illustrated in FIG. 4. A single resonance was observed for the aromatic protons and the NH groups showed a broadened resonance at 4.78 ppm. The methylene groups are diastereotopic and so, four broadened resonances were observed from 3.32-2.46 ppm, each with an integral of 4H. The tert-butyl and acetate methyl groups resonate as singlets with integrals of 18H and 6H, respectively. The methyl groups on the ligand backbone are also diastereotopic and are observed as two singlets, each with a relative integral of 6H.

Figure 1:
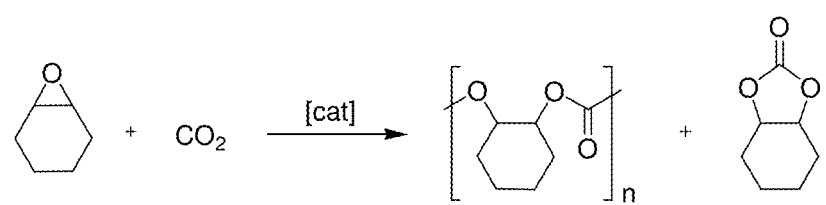
FIG. 1 shows the copolymerization of carbon dioxide and cyclohexene oxide, where [cat]=catalyst, frequently a Zn(II), Cr(III) or Co(III) complex.

The complex was tested, under very mild conditions, for the copolymerization of carbon dioxide and cyclohexene oxide as illustrated in FIG. 1. Results of the copolymerization are set out in table 1 below. Thus, at only 1 atm pressure of carbon dioxide and at $70°$ C., poly(cyclohexene carbonate) was produced with a TON of 300 and a TOF of 12 $h^{-1}$. On increasing the temperature to $100°$ C. (Table 1, 1-4), the TON increased to 530 and the TOF to 26 $h^{-1}$. There are very few catalysts which are effective at such low pressure, the most active of these is a dizinc complex with a TON of 20 and TOF of 3.3 $h^{-1}$ (Table 1, entry 9). $[L^1Zn_2(OAc)_2]$ is also tolerant, it operates effectively at a loading of 0.01 mol % (Table 1, entries 5-9). The catalyst shows much enhanced activity at 1 atm compared to any previously reported catalysts; it has TONs which are up to 35 times greater and TOFs up to 10 times greater (entry 10). Indeed $[L^1Zn_2$ (OAc)$_2$] displays comparable TONs and TOFs to Darensbourg's bis(phenoxide)zinc catalysts (entry 12), but at 1/60 of the pressure of carbon dioxide. When the pressure of CO$_2$ was increased (entries 7-9), the TONs and TOFs increased to a maximum of 3400 and 140 h$^{-1}$, respectively. Indeed, under comparable conditions (70° C., 7 atm), [L$^1$Zn$_2$OAc$_2$] has a slightly higher TON (entry 7) than Coates β-diiminate catalysts (entry 11).

Analytical (VG) Autospec spectrometer. Elemental analyses were determined by Mr Stephen Boyer at London Metropolitan University, North Campus, Holloway Road, London, N7. SEC data were collected using a Polymer labs PL GPC-50 instrument with THF as the eluent, at a flow rate of 1 mLmin$^{-1}$. Two Polymer labs Mixed D columns were used in series. Narrow M$_w$ polystyrene standards were used to calibrate the instrument.

TABLE 1

The copolymerization of carbon dioxide and cyclohexene oxide, catalysed by [L$^1$Zn$_2$(OAc)$_2$].

| Entry # | T (° C.) | p(CO$_2$) [atm] | TON$^{a)}$ | TOF$^{b)}$ [h$^{-1}$] | % carbonate$^{c)}$ | % polymer$^{d)}$ | M$_n$$^{e)}$ | PDI$^{e)}$ |
|---|---|---|---|---|---|---|---|---|
| 1 | 70 | 1 | 292 | 12.2 | >99 | >99.6 | 3518 | 1.22 |
| 2 | 80 | 1 | 439 | 18.3 | >99 | 96 | 6193 | 1.19 |
| 3 | 90 | 1 | 567 | 23.6 | >99 | 95 | 6519 | 1.21 |
| 4 | 100 | 1 | 527 | 25.1 | >99 | 94 | 7358 | 1.21 |
| 5$^{f)}$ | 70 | 1 | 321 | 13.4 | >99 | >99 | N/A | N/A |
| 6$^{f)}$ | 100 | 1 | 708 | 29.5 | >99 | 89 | 1395 | 1.19 |
| 7$^{f)}$ | 70 | 7 | 728 | 30.3 | >99 | >99 | 1861 | 1.23 |
| 8$^{f)}$ | 70 | 10 | 760 | 31.6 | >99 | >99 | 2585 | 1.24 |
| 9$^{f)}$ | 100 | 10 | 3347 | 139.5 | >99 | 95 | 14100$^{g)}$ | 1.03 |
| 10) Comparative example | 60 | 1 | 20 | 3.3 | >99 | N/A | 19200 | 1.56 |
| 12) Comparative example | 50 | 7 | 494 | 247 | 90 | N/A | 31000 | 1.10 |
| 11) Comparative example | 80 | 60 | 774 | 32.2 | >99 | N/A | 8900 | 1.2 |

The copolymerizations were conducted in a Schlenk tube for 20-24 h, at a loading of [L$^1$Zn$_2$(OAc)$_2$]:cyclohexene oxide of 1:1000 (unless otherwise stated), or in a Parr reactor at 7-10 atm for 24 h (entries 7-9).
$^{a)}$the turn over number (TON) = number of moles of cyclohexene oxide consumed/number of moles of [L$^1$Zn$_2$(OAc)$_2$].
$^{b)}$the turn over frequency (TOF) = TON/reaction period.
$^{c)}$determined by integration of the signal at 3.45 ppm assigned to poly(cyclohexene ether) in the $^1$H NMR spectrum.
$^{d)}$assigned by integration of the signal at 4.65 ppm assigned to cyclohexene carbonate.
$^{e)}$determined by GPC in THF, using narrow M$_w$ polystyrene standards.
$^{f)}$carried out at a loading of [L$^1$Zn$_2$(OAc)$_2$]:cyclohexene oxide of 1:10 000.
$^{g)}$a bimodal peak was observed with M$_n$ of 14100 and 6600.

Figure 3:
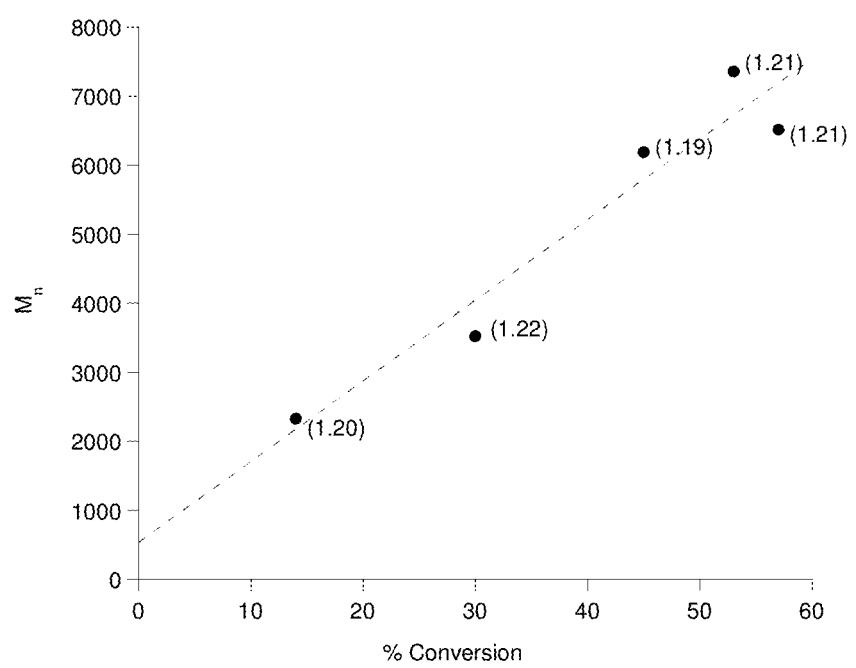
FIG. 3 shows a plot showing the $M_n$ of the polycarbonate, as determined by GPC, versus the percentage conversion, as determined by $^1$H NMR. The values in parentheses represent the polydispersity index.

The catalyst is also selective, yielding a polymer with >99% polycarbonate linkages. In contrast to previous literature catalysts, [L$^1$Zn$_2$(OAc)$_2$] is remarkably robust, it is still active after 24 h of reaction and at loadings of 0.01 mol %. It is also stable in air; indeed comparable TONs and TOFs are obtained for polymerizations when [L$^1$Zn$_2$(OAc)$_2$] is handled in air. The polymerization is well controlled, giving polycarbonate with a narrow polydispersity index (Table 1) and a linear relationship between the M$_n$ and percentage conversion (as illustrated in FIG. 3).

Materials and Methods

All reactions were conducted under a nitrogen atmosphere, using either standard anaerobic techniques or in a nitrogen filled glovebox. High-pressure reactions were carried out in a Parr 5513 100 mL bench reactor. 4-tert-butyl-2,6-diformylphenol was synthesised according to a literature procedure. All solvents and reagents were obtained from commercial sources (Aldrich and Merck). THF was distilled from sodium and stored under nitrogen. Cyclohexene oxide, methylene chloride and d$_2$-TCE were distilled from CaH$_2$ and stored under nitrogen. CP grade carbon dioxide was used for polymerisation studies.

$^1$H and $^{13}$C {$^1$H}NMR spectra were performed on a Bruker AV-400 instrument, unless otherwise stated. All mass spectrometry measurements were performed using a Fisons Synthesis of [H$_4$L$^{1'}$](ClO$_4$)$_2$

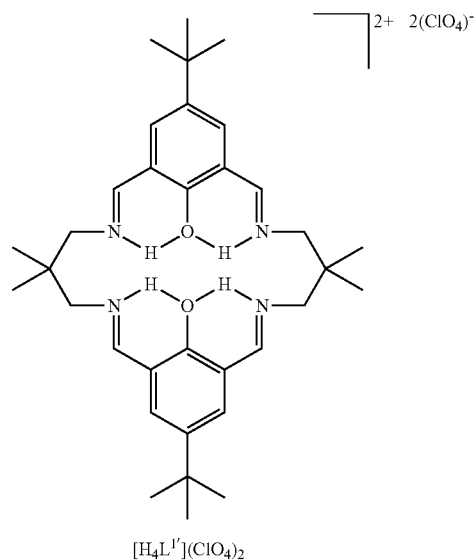

[H$_4$L$^{1'}$](ClO$_4$)$_2$

To a round-bottomed flask was added 4-tert-butyl-2,6-diformylphenol (1.20 g, 5.80 mmol), NaClO$_4$ (2.81 g, 23.2 mmol), acetic acid (0.66 mL, 11.6 mmol) and methanol (90 mL). This solution was heated to 70° C. whilst stirring, as the solution started to boil, 2,2-dimethyl-1,3-propanediamine (0.70 mL, 5.8 mmol) was added slowly in methanol (30 mL). The yellow reaction mixture was allowed to cool to room temperature, and left stirring for 72 hours, after which a bright orange precipitate was filtered and washed with cold (−78° C.) methanol (1.85 g, 95%).

$\delta_H$(400 MHz; $d^6$-dmso) 13.61 (4H, br s, NH/OH), 8.68 (4H, d, N═CH), 7.66 (4H, s, Ar—H), 3.87 (8H, s, $CH_2$), 1.28 (12H, s, $CH_3$), 1.15 (18H, s, $CH_3$); $\delta_C$(400 MHz; $d^6$-dmso) 176.5, 169.3, 142.5, 136.2, 116.6, 60.7, 35.2, 34.0, 31.2 and 23.6.

Synthesis of $H_2L^1$ $[H_4L^1](ClO_4)_2$ (1.80 g, 2.69 mmol) was suspended in methanol (180 mL). The suspension was cooled to 0° C. and $NaBH_4$ (2.65 g, 69.9 mmol) was added slowly. As $NaBH_4$ was added, the red-orange suspension turned to a clear solution. Water was added slowly, and the solution turned cloudy. Once precipitate started to form, the mixture was left overnight and $H_2L^1$ was filtered off as a white solid (1.21 g, 88%).

Mp 162° C. (from methanol); Anal. Calc. for $C_{34}H_{56}N_4O_2$: C, 73.87; H, 10.21; N, 10.13. Found: C, 73.87; H, 10.26; N, 10.18; $\delta_H$(400 MHz; $CDCl_3$): 6.95 (s, 4H, Ar—H), 3.76 (s, 8H, $CH_2$), 2.53 (s, 8H, $CH_2$), 1.27 (s, 18H, $CH_3$), 1.02 (s, 12H, $CH_3$); $\delta_C$(400 MHz; $CDCl_3$) 154.7, 140.7, 124.9, 124.3, 59.9, 53.4, 34.7, 34.1, 33.9, 31.7, and 25.2; m/z (ES) 553 ($M^+$, 75%), 277 (100), 216 (8), 175 (7).

Synthesis of $[L^1Zn_2OAc_2]$ $H_2L^1$ (0.40 g, 0.72 mmol) was dissolved in dry THF (10 mL) and transferred into a Schlenk tube containing KH (0.04 g, 1.08 mmol), and cooled to −78° C., under nitrogen. This suspension was allowed to warm to room temperature and left to stir for 1 hour. The excess KH was filtered off and the solution transferred to a Schlenk tube containing $Zn(OAc)_2$ (0.27 g, 1.48 mmol). The reaction was left to stir for 16 hours overnight, after which the THF was removed in vacuo, and the product taken up in dry $CH_2Cl_2$ (10 mL). This was then filtered and the $CH_2Cl_2$ removed in vacuo to yield the title compound as a white powder (0.40 g, 69.5%).

Anal. Calc. for $C_{36}H_{60}N_4O_2Zn_2$: C, 57.07; H, 7.56; N, 7.01. Found: C, 56.91; H, 7.46; N, 6.92; $\delta_H$ (400 MHz, $d^2$-tce, 383 K) 7.00 (4H, s, Ar—H), 4.78 (4H, br s, NH), 3.32 (4H, br d, $CH_2$), 2.95 (4H, br s, $CH_2$), 2.84 (4H, br s, $CH_2$) 2.46 (~4H, br s, $CH_2$), 2.08 (~6H, s, OAc), 1.35 (18H, s, Ar—C—$CH_3$), 1.29 (6H, s, $CH_2$—C—$CH_3$), 1.05 (6H, s, $CH_2$—C—$CH_3$); $\delta_C$ (400 MHz, $d^2$-tce, 383 K) 174.7, 159.5 (br), 139.5 (br), 127.4, 124.4, 63.2, 56.3, 33.5, 31.4, 27.9, 21.1 and 20.7; m/z (FAB) 739 ($[M-OAc]^+$, 100%).

Polymerization Conditions

Cyclohexene oxide (5 mL, 49.4 mmol) and $[L^1Zn_2(OAc)_2]$ (0.049 mmol) were added to a Schlenk tube. The cyclohexene oxide was degassed, before being left stirring under 1 atm $CO_2$, at a certain temperature, for 24 hours. The crude reaction mixture was then taken up in $CH_2Cl_2$ and evaporated in air, after which the product was dried in vacuo overnight.

For high-pressure reactions, $[L^1Zn_2(OAc)_2]$ (0.0198 mmol) was dissolved in cyclohexene oxide (20 mL, 197.6 mmol) in a Schlenk tube. This was transferred into the Parr reaction vessel, (which was dried in an oven at 140° C. overnight) under nitrogen. The reactor was brought up to temperature under 2 atm $CO_2$ before being left at a certain pressure and temperature for 24 hours. Work-up as above.

Turn-over-number calculated as [(isolated yield—weight catalyst)/142.1]/moles catalyst.

Example 2

Complexes $[L^2Zn_2(OAc)_2]$ and $[L^3Zn_2(OAc)_2]$ were prepared in the same manner as $[L^1Zn_2(OAc)_2]$.

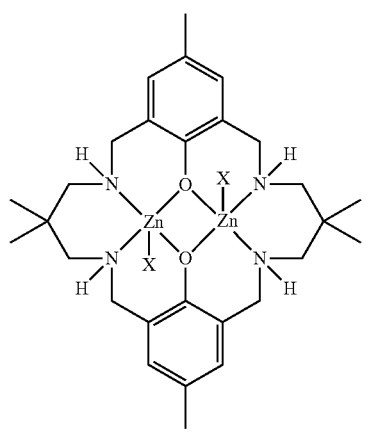

$L^2Zn_2(OAc)_2$

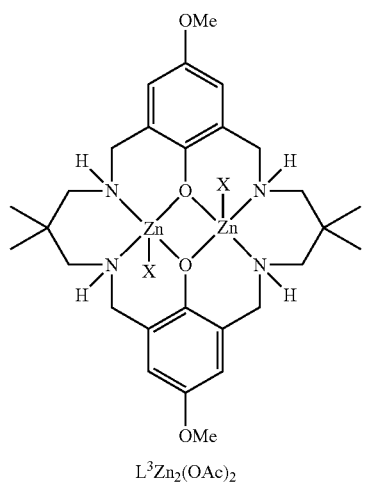

$L^3Zn_2(OAc)_2$

Both complexes were found to react with cyclohexene oxide in the same manner as $[L^1Zn_2(OAc)_2]$. The nature of the complexes was confirmed by very similar features in the $^1H$ and $^{13}C$ NMR spectra, elemental analysis and FAB mass spectra to $[L^1Zn_2(OAc)_2]$.

Both $[L^2Zn_2(OAc)_2]$ and $[L^3Zn_2(OAc)_2]$ were tested under mild conditions (80° C., 1 atm $CO_2$, 24 hours), for the copolymerisation of carbon dioxide and cyclohexene oxide. Results showed both complexes to have similar activity to $[L^1Zn_2(OAc)_2]$. Results of the copolymerisation are set out in table 2.

TABLE 2

Comparison of catalytic activity between [L$^{1,2,3}$Zn$_2$(OAc)$_2$] at 80° C., 1 atm CO$_2$, 24 hours.

| Catalyst | TON | TOF [h$^{-1}$] | % carbonate | % polymer | Mn | PDI | % conversion |
|---|---|---|---|---|---|---|---|
| L$^1$Zn$_2$OAc$_2$ | 439 | 18.4 | >99 | 96 | 6200 | 1.20 | 45 |
| L$^2$Zn$_2$OAc$_2$ | 398 | 16.6 | >99 | 96 | 5800 | 1.21 | 40 |
| L$^3$Zn$_2$OAc$_2$ | 288 | 12 | >99 | 97 | 2800 | 1.21 | 29 |

Molar ratio of catalyst:cyclohexene oxide - 1:1000

[L$^2$Zn$_2$(OAc)$_2$] was also tested at a higher temperature and pressure (100° C., 10 atm CO$_2$, 24 hours) and was found to exhibit very similar activities to [L$^1$Zn$_2$(OAc)$_2$] under these conditions. These results are outlined in table 3 below.

TABLE 3

Comparison of catalytic activity between [L$^{1,2}$Zn$_2$(OAc)$_2$] at 100° C., 10 atm CO$_2$, 24 hours.

| Catalyst | TON | TOF [h$^{-1}$] | % carbonate | % polymer | Mn | PDI |
|---|---|---|---|---|---|---|
| L$^1$Zn$_2$(OAc)$_2$ | 3347 | 140 | >99 | 96 | 14100 | 1.03 |
| L$^2$Zn$_2$(OAc)$_2$ | 2839 | 118 | >99 | 96 | 13000 | 1.04 |

Molar ratio of catalyst:cyclohexane oxide - 1:10000

General Procedure for the Synthesis of [H$_4$L″](ClO$_4$)$_2$

To a round-bottomed flask was added 4-R$_1$-2,6-diformylphenol, wherein R$_1$ is as defined for formula (I), (5.80 mmol), NaClO$_4$ (2.81 g, 23.2 mmol), acetic acid (0.66 mL, 11.6 mmol) and methanol (90 mL). This solution was heated to 70° C. whilst stirring, as the solution started to boil, 2,2-dimethyl-1,3-propanediamine (0.70 mL, 5.8 mmol) was added slowly in methanol (30 mL). The reaction mixture was allowed to cool to room temperature, and left stirring for 24 hours, after which a precipitate was filtered and washed with cold (−78° C.) methanol.

This procedure was carried out to produce [H$_4$L$^2$](ClO$_4$)$_2$ wherein R$_1$ is methyl, and to produce [H$_4$L$^3$](ClO$_4$)$_2$ wherein R$_1$ is methoxy.

[H$_4$L$^2$](ClO$_4$)$_2$ (orange crystals; 1.72 g, 2.26 mmol, 76%): $^1$H NMR (d$_6$-DMSO): δ8.63 (d, J=13.5 Hz, 4H, N═CH), 7.34 (s, 4H, Ar—H), 3.90 (d, 8H, N—CH$_2$—C), 2.13 (s, 6H, Ar—CH$_3$), 1.28 (s, 12H, C—CH$_3$). $^{13}$C{$^1$H}NMR (d$_6$-DMSO): δ 176.1, 168.1, 145.2, 122.5, 116.3, 60.2, 33.7, 30.4, 18.7. Anal. Calc. for C$_{28}$H$_{38}$Cl$_2$N$_4$O$_{10}$: C, 50.84; H, 5.79; N, 8.47. Found: C, 50.79; H, 5.77; N, 8.41.

[H$_4$L$^3$](ClO$_4$)$_2$ (brick red powder; 0.63 g, 0.90 mmol, 31%): $^1$H NMR (d$_6$-DMSO): δ 13.83 (s, 4H, OH/NH), 8.67 (d, 4H, N═CH), 7.22 (s, 4H, Ar—H), 3.90 (s, 8H, N—CH$_2$—C), 3.69 (s, 6H, Ar—O—CH$_3$), 1.29 (s, 12H, C—CH$_3$). $^{13}$C{$^1$H}NMR ((d$_6$-DMSO): δ 174.3, 168.5, 147.3, 130.7, 116.9, 61.2, 56.4, 34.4, 23.5. Anal. Calc. for C$_{28}$H$_{38}$C$_{12}$N$_4$O$_{12}$: C, 48.49; H, 5.52; N, 8.08. Found: C, 48.47; H, 5.46; N, 8.12.

Synthesis of H$_2$L$^2$

[H$_4$L$^2$](ClO$_4$)$_2$ (2.7 mmol) was suspended in methanol (180 mL). The suspension was cooled to 0° C. and NaBH$_4$ (2.65 g, 70 mmol) was added slowly. As NaBH$_4$ was added, the red-orange suspension turned to a clear solution. The solution was allowed to stir at room temperature for 1 hour, after which water was added slowly, and the solution turned cloudy. Once precipitate started to form, the mixture was left overnight. The product was filtered, washed with water and dried under vacuum to yield white crystals of the title compound.

H$_2$L$^2$ (0.75 g, 1.6 mmol, 59%): Mp 154° C. $^1$H NMR (CDCl$_3$): δ 6.74 (s, 4H, Ar—H), 3.74 (s, 8H, N—CH$_2$—Ar), 2.51 (s, 8H, N—CH$_2$—C), 2.22 (s, 6H, Ar—CH$_3$), 1.03 (s, 12H, C—CH$_3$). $^{13}$C{$^1$H}NMR (CDCl$_3$): δ 154.6, 128.7, 127.2, 124.7, 59.7, 52.7, 34.7, 25.0, 20.4. m/z (ES): 469 ([M+H]$^+$, 100%), 235 (14%). Anal. Calc. for C$_{28}$H$_{44}$N$_4$O$_2$: C, 71.76; H, 9.46; N, 11.95. Found: C, 71.60; H, 9.52; N, 11.88.

Synthesis of H$_2$L$^3$

[H$_4$L$^3$](ClO$_4$)$_2$ (1.40 g, 2.02 mmol) was suspended in MeOH (110 mL). The suspension was cooled to 0° C. and NaBH$_4$ (1.99 g, 52.6 mmol) was added slowly. As NaBH$_4$ was added, the brick-red suspension turned to a light brown, clear solution. The solvent was removed in vacuo and the crude product taken up in a minimal amount of CHCl$_3$. After an hour a brown precipitate was filtered off, and the solvent removed in vacuo. The product was recrystallised from MeOH/H$_2$O and dried under vacuum.

H$_2$L$^3$ (White crystals, 0.340 g, 0.68 mmol, 34% yield): Mp 74° C. (from CHCl$_3$). $^1$H NMR (CDCl$_3$): δ 6.52 (s, 4H, Ar—H), 3.74 (m, 14H, N—CH$_2$—Ar and Ar—O—CH$_3$), 2.50 (s, 8H, N—CH$_2$—C), 1.02 (s, 12H, C—CH$_3$). $^{13}$C{$^1$H}NMR (CDCl$_3$): δ 151.7, 150.5, 125.6, 113.5, 59.4, 55.7, 52.6, 34.6, 24.9; m/z (ES): 501 (100%, [M+H]$^+$), 251 (25%). Anal. Calc. for C$_{28}$H$_{44}$N$_4$O$_4$: C, 67.17; H, 8.86; N, 11.19. Found: C, 67.28; H, 8.98; N, 11.06.

General Procedure for the Synthesis of [L″Zn$_2$(OAc)$_2$]

H$_2$L″ (0.72 mmol) was dissolved in dry THF (10 mL) in a Schlenk tube. The solution was transferred to another Schlenk tube containing Zn(OAc)$_2$ (0.27 g, 1.48 mmol). The reaction was left to stir for 16 hours overnight, after which the THF was removed in vacuo, and the product taken up in dry CH$_2$Cl$_2$ (10 mL). The solution was then filtered, solvent removed in vacuo and the white powdery product dried under vacuum overnight.

[L$^2$Zn$_2$(OAc)$_2$] (0.37 g, 0.52 mmol, 72%): $^1$H NMR (d$_2$-TCE, 383 K): δ 6.83 (s, 4H, Ar—H), 4.76 (br s, 4H, NH), 3.26 (br s, 4H, CH$_2$), 2.96 (br s, 4H, CH$_2$), 2.79 (br s, 4H, CH$_2$), 2.44 (br s, 4H, CH$_2$), 2.27 (s, 6H, Ar—CH$_3$), 2.09 (s, 6H, OAc), 1.26 (s, 6H, C—CH$_3$), 1.04 (s, 6H, C—CH$_3$). $^{13}$C{$^1$H}NMR (d$_2$-TCE, 383 K): δ 175.1, 159.0 (br), 139.0 (br), 131.0, 124.7, 63.4, 56.1, 33.4, 27.9, 21.3, 19.7. m/z (FAB): 656 ([M-OAc]$^+$, 100%). Anal. Calc. for C$_{32}$H$_{48}$N$_4$O$_6$Zn$_2$: C, 53.71; H, 6.76; N, 7.83. Found: C, 53.60; H, 6.74; N, 7.82.

[L$^3$Zn$_2$(OAc)$_2$] (0.40 g, 0.54 mmol, 75%): $^1$H NMR (d$_2$-TCE, 383 K): δ 6.61 (s, 4H, Ar—H), 4.68 (s, br, 4H, NH), 3.77 (s, 6H, Ar—OCH$_3$), 3.21 (s, br, 4H, CH$_2$), 2.98 (s, br, 4H, CH$_2$), 2.76 (s, br, 4H, CH$_2$), 2.49 (s, br, 4H, CH$_2$), 2.01 (s, 6H, OAc), 1.25 (s, 6H, C—CH$_3$), 1.03 (s, 6H, C—CH$_3$). $^{13}$C{$^1$H}NMR (d$_2$-TCE, 383 K): δ 174.5, 155.2, 150.4, 125.5, 116.2, 63.2, 56.8, 33.4, 27.8, 21.4, 20.8. m/z (FAB): 687 ([M-OAc]$^+$, 98%). Anal. Calc. for C$_{32}$H$_{48}$N$_4$O$_8$Zn$_2$: C, 51.42; H, 6.47; N, 7.49. Found: C, 51.36; H, 6.56; N, 7.49.

Example 3

Figure 5:
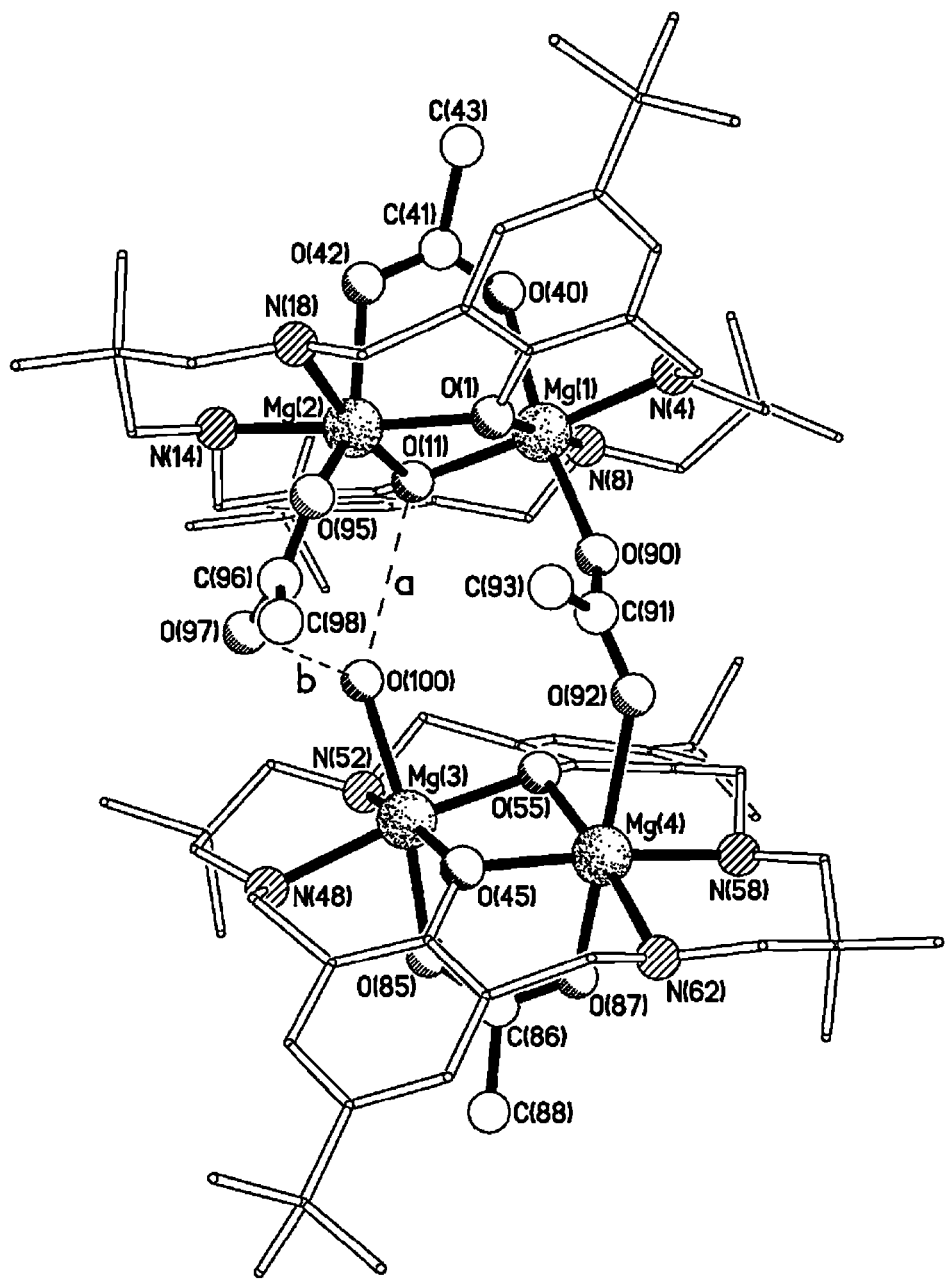
FIG. 5 shows an X-ray crystallography structure for the dimeric catalyst complex $[L^1{}_2Mg_4(OAc)_4(H_2O)]$ The present invention will now be illustrated by reference to one or more of the following non-limiting examples.

A complex of $H_2L^1$ and $Mg(OAc)_2$ was prepared in the same manner as $[L^1Zn_2(OAc)_2]$. X-ray crystallography, $^1H$ and $^{13}C$ NMR data suggest that the bimetallic magnesium complex produced is a mixture of two different structures, one containing two acetate groups ($[L^1Mg_2(OAc)_2]$) and one being a dimeric structure containing two ligand moieties linked by a bridging acetate group, with one bound water molecule ($[L^1{}_2Mg_4(OAc)_3(H_2O)]$). The dimeric structure is shown in FIG. 5. The dimeric structure is formed due to the presence of an impurity of water during the complexation of the macrocyclic ligand $H_2L^1$ with $Mg(OAc)_2$. Unlike $Zn(OAc)_2$, $Mg(OAc)_2$ is not commercially available in anhydrous form. Commercially available $Mg(OAc)_2.4H_2O$ was dried under vacuum at 100° C., prior to use in the complexation reaction. It has been found that this drying was insufficient to remove all of the water, and therefore provides a source of water to allow the formation of a dimeric complex.

Other catalyst complexes of formula (I) of the present invention may form a dimeric structure or mixture of monomer and dimer where catalyst synthesis is carried out in the presence of water. Dimer formation is avoided when the synthesis is anhydrous.

The mixture of the $[L^1Mg_2(OAc)_2]$ complex and dimeric structure thereof was tested under mild conditions for the copolymerisation of carbon dioxide and cyclohexane oxide. Results of the copolymerisation are set out in table 4. Data shows that the magnesium complex mixture shows excellent activity under identical conditions as used for $[L^1Zn_2(OAc)_2]$.

TABLE 4

Comparison of $[L^1Zn_2(OAc)_2]$ and magnesium complex activities for copolymerization of cyclohexene oxide and $CO_2$. Where $[L^1Mg_2(OAc)_2]$ represents a mixture of $[L^1Mg_2(OAc)_2]$ and $[L^1{}_2Mg_4(OAc)_3(H_2O)]$. The molar catalyst loading is 1:1000 (catalyst:epoxide) at 1 atm $CO_2$ and 1:10000 (catalyst:epoxide) at 10 atm $CO_2$.

| Catalyst | Time (h) | T (° C.) | P (atm) | TON | TOF [h$^{-1}$] | % carbonate | % polymer | Mn | PDI |
|---|---|---|---|---|---|---|---|---|---|
| $L^1Zn_2(OAc)_2$ | 24 | 80 | 1 | 439 | 18.3 | >99 | 96 | 6200 | 1.19 |
| $L^1Mg_2(OAc)_2$ | 16 | 80 | 1 | 527 | 33.3 | >99 | >99 | 7200 | 1.23 |
| $L^1Zn_2(OAc)_2$ | 24 | 100 | 1 | 527 | 25.1 | >99 | 94 | 7400 | 1.21 |
| $L^1Mg_2(OAc)_2$ | 5 | 100 | 1 | 482 | 96.4 | >99 | >99 | 6400 | 1.24 |
| $L^1Zn_2(OAc)_2$ | 24 | 100 | 10 | 3347 | 140 | >99 | 96 | 14100 | 1.03 |
| $L^1Mg_2(OAc)_2$ | 5 | 100 | 10 | 3660 | 732 | >99 | >99 | 14300 | 1.05 |

As can be seen from table 4, the magnesium catalyst mixture shows a TOF of almost 34 h$^{-1}$ at 80° C. and 1 atm $CO_2$, this value increases to almost 97 h$^{-1}$ when the temperature is increased to 100° C. (entries 2 and 4). If the pressure is increased to 10 atm, the activity is increased further still (entry 6). In addition, there is no evidence for the formation of any cyclic carbonate in the $^1H$ NMR spectra. This is observed for all copolymerisations using the magnesium catalyst and is very unusual, as the formation of cyclic carbonate is generally held to be under thermodynamic control, increasing with temperature. The polymer properties are very similar to those produced by $[L^1Zn_2(OAc)_2]$, with similar polydispersities, molecular weights and no observable ether linkages.

Synthesis of the Mixed Magnesium Complex $H_2L^1$ (0.40 g, 0.72 mmol) was dissolved in dry THF (10 mL) in a Schlenk tube The solution was transferred to another Schlenk tube containing $Mg(OAc)_2$ (0.21 g, 1.48 mmol). The reaction was left to stir for 16 hours overnight, after which the THF was removed in vacuo, and the product taken up in dry $CH_2Cl_2$ (10 mL). The solution was then filtered, the solvent removed in vacuo and the white powdery product dried under vacuum overnight.

$^1H$ NMR (CD$_3$OD): δ Complex A (monomeric $[L^1Mg_2(OAc)_2]$): 7.03 (s, 4H, Ar—H), 4.03 (d, J=11.8 Hz, 4H, CH$_2$), 3.22 (d, J=11.8 Hz, 4H, CH$_2$). 2.79 (d, J=11.6 Hz, 4H, CH$_2$), 2.65 (d, J=11.5 Hz, 4H, CH$_2$), 1.91 (s, ~6H, OAc), 1.28 (s, 18H, Ar—C—CH$_3$), 1.26 (s, 6H, C—C—CH$_3$), 1.03 (s, 6H, C—C—CH$_3$). Complex B (dimeric complex $[L^1{}_2Mg_4(OAc)_4(H_2O)]$): 7.14 (s, 4H, Ar—H), 3.97 (s, 8H, Ar—CH$_2$—N), 2.73 (s, 8H, N—CH$_2$—C), 1.91 (s, ~6H, OAc), 1.29 (s, 18H, Ar—C—CH$_3$), 1.26 (s, ~6H, C—C—CH$_3$), 1.06 (s, 6H, C—C—CH$_3$). m/z (FAB): 657 ([M-OAc]$^+$, 100%).

The invention claimed is:
1. A process comprising copolymerizing carbon dioxide with an epoxide in the presence of a catalyst of formula (I) to prepare a polycarbonate, wherein the catalyst of formula (I) has the structure:

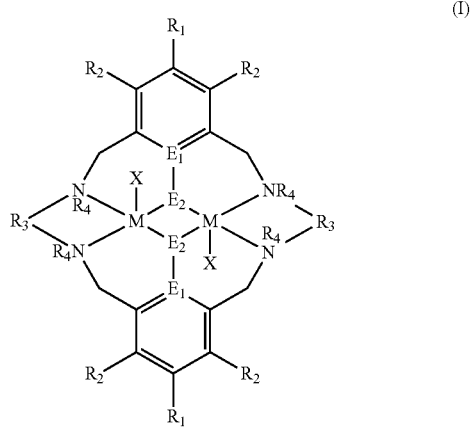

wherein $R_1$ and $R_2$ are independently hydrogen, alkyl, haloalkyl, aryl, halide, amine, a nitro group, an ether group, a silyl ether group, a nitrile group or an acetylide group;

$R_3$ is alkylene, arylene or cycloalkylene;

$R_4$ is H, alkyl, aryl alkylaryl;

$E_1$ is C, $E_2$ is O, S or NH or $E_1$ is N and $E_2$ is O;

X is $OCOCH_3$, $OCOCF_3$, $OSO_2C_7H_7$, $OSO(CH_3)_2$, alkyl, alkoxy, halide or amido; and M is Zn(II), O(II), Co(II), Mg(II), Fe(II), Cr(III)-X, Co(III)-X, or Fe(III)-X.

2. The process according to claim 1, wherein the epoxide is selected from cyclohexene oxide, propylene oxide, a substituted cyclohexene oxide, an alkylene oxide or a substituted oxirane.

3. The process as claimed in claim 1, wherein said process is carried out at 1 atmosphere.

4. The process according to claim 1, wherein $R_1$ and $R_2$ are independently selected from hydrogen, tBu, Me, $CF_3$, phenyl, F, Cl, Br, I, $NMe_2$, $NEt_2$, $NO_2$, OMe, $OSiMe_3$, $OSiEt_3$, CNMe, CN and CCPh.

5. The process according to claim 1, wherein $R_3$ is a substituted or unsubstituted $C_3$ alkylene group.

6. The process according to claim 1, wherein $R_3$ is ethylene, 2,2-dimethylpropylene, propylene, butylene, phenylene, cyclohexylene or biphenylene.

7. The process according to claim 1, wherein $R_4$ is H, Me, Et, Bn, iPr, tBu or Ph.

8. The process according to claim 1, wherein X for the catalyst of formula (I) is $OCOCH_3$, $OCOCF_3$, $OSO_2C_7H_7$, $OSO(CH_3)_2$, Et, Me, PhOEt, OMe, OiPr, OtBu, Cl, Br, I, F, $N(iPr)_2$ or $N(SiMe_3)_2$.

9. The process according to claim 1, wherein said catalyst of formula (I) has a structure selected from:

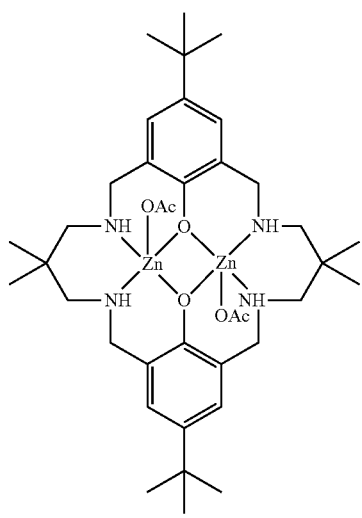

$[L^1Zn_2(OAc)_2]$

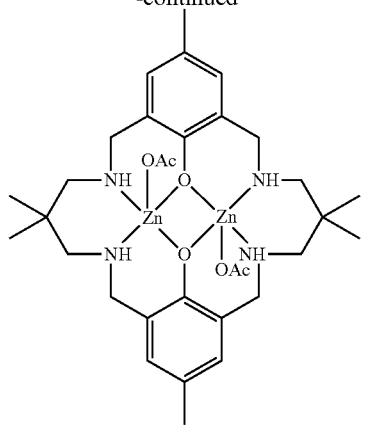

$[L^2Zn_2(OAc)_2]$

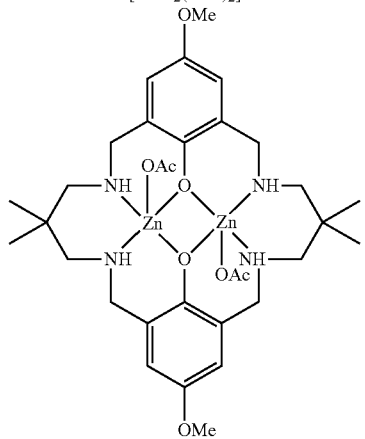

$[L^3Zn_2(OAc)_2]$

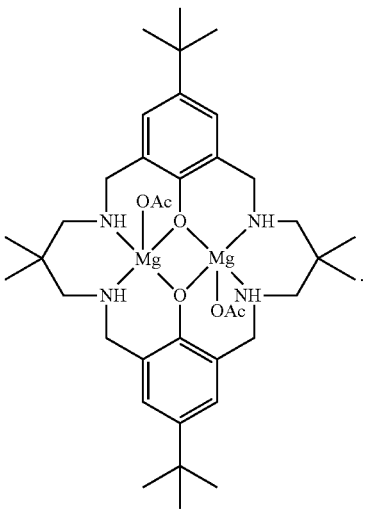

$[L^1Mg_2(OAc)_2]$

* * * * *

UNITED STATES PATENT AND TRADEMARK OFFICE
CERTIFICATE OF CORRECTION

| | | |
|---|---|---|
| PATENT NO. | : 9,994,675 B2 | Page 1 of 1 |
| APPLICATION NO. | : 14/526017 | |
| DATED | : June 12, 2018 | |
| INVENTOR(S) | : Charlotte Katherine Williams et al. | |

It is certified that error appears in the above-identified patent and that said Letters Patent is hereby corrected as shown below:

In the Claims

Column 19, Lines 10-11, the text: "M is Zn(II), O(II), Co(H), Mg(II), Fe(II), Cr(III)-X, Co(III)-X, or Fe(III)-X" should be replaced with: --M is Zn(II), Cr(II), Co(II), Mg (II), Fe(II), Cr (III)-X, Co (III)-X, or Fe(III)-X--.

Signed and Sealed this
Nineteenth Day of February, 2019

Andrei Iancu
*Director of the United States Patent and Trademark Office*